US012758129B2

(12) United States Patent
Hu

(10) Patent No.: US 12,758,129 B2
(45) Date of Patent: Oct. 13, 2026

(54) IMPACT TYPE BLOOD COLLECTION APPARATUS, NEGATIVE PRESSURE BLOOD COLLECTION PEN AND BLOOD COLLECTION METHOD

(71) Applicant: Promisemed Hangzhou Meditech Co., Ltd., Hangzhou City (CN)

(72) Inventor: Chaoyu Hu, Hangzhou City (CN)

(73) Assignee: PROMISEMED HANGZHOU MEDITECH CO., LTD., Hangzhou City (CN)

( * ) Notice: Subject to any disclaimer, the term of this patent is extended or adjusted under 35 U.S.C. 154(b) by 856 days.

(21) Appl. No.: 18/275,683

(22) PCT Filed: Oct. 8, 2021

(86) PCT No.: PCT/CN2021/122627

§ 371 (c)(1),
(2) Date: Aug. 3, 2023

(87) PCT Pub. No.: WO2022/073476

PCT Pub. Date: Apr. 14, 2022

(65) Prior Publication Data

US 2024/0099619 A1 Mar. 28, 2024

(30) Foreign Application Priority Data

Oct. 9, 2020 (CN) ......................... 202011073440.1
Oct. 9, 2020 (CN) ......................... 202011073464.7
(Continued)

(51) Int. Cl.
*A61B 5/151* (2006.01)
*A61B 5/15* (2006.01)

(52) U.S. Cl.
CPC ........ *A61B 5/151* (2013.01); *A61B 5/150099* (2013.01); *A61B 5/150412* (2013.01)

(58) Field of Classification Search
CPC ........ A61B 5/150022; A61B 5/150099; A61B 5/150145; A61B 5/15019;
(Continued)

(56) References Cited

U.S. PATENT DOCUMENTS

2009/0299224 A1* 12/2009 Yoo ................. A61B 5/150503
600/583

FOREIGN PATENT DOCUMENTS

CN 102245104 A 11/2011
CN 102802524 A 11/2012
(Continued)

*Primary Examiner* — Mohamed G Gabr
(74) *Attorney, Agent, or Firm* — Muncy, Geissler, Olds & Lowe, P.C.

(57) ABSTRACT

The present invention relates to the technical field of medical instruments, and particularly discloses an impact type blood collection apparatus, a negative pressure blood collection pen and a blood collection method. The impact type blood collection apparatus includes a base, a front cover, a needle stand, a first elastic element and an impact block. The impact block at least has a first state in which the impact block is attached to a tail end of the needle stand and a second state in which the impact block is separated from the tail end of the needle stand, and the impact block stores energy in the second state and is configured to move from the second state to the first state and then drive the needle stand to move from a first position to a puncture position through impact. In the above structure, during the process of the impact block moving to a state to be triggered, the needle stand is maintained in the first position, which changes the technical concept that the state of the needle stand in the prior art will change with an armed state to be triggered, so that the route of the needle stand is relatively short, and the puncture stability and puncture accuracy are higher. During the process of replacing a disposable blood collection needle, the needle stand is maintained in the first position,
(Continued)

thereby avoiding the ineffective work of an elastic element and being conducive to prolonging the service life of a blood collection pen.

16 Claims, 25 Drawing Sheets

(30) Foreign Application Priority Data

Oct. 9, 2020 (CN) ......................... 202011074868.8
Oct. 9, 2020 (CN) ......................... 202011075157.2

(58) Field of Classification Search
CPC ........ A61B 5/150213; A61B 5/150412; A61B 5/151; A61B 5/15111; A61B 5/15117; A61B 5/15123; A61B 5/1513; A61B 5/15144
See application file for complete search history.

(56) References Cited

FOREIGN PATENT DOCUMENTS

| | | | |
|---|---|---|---|
| CN | 105455824 | A | 4/2016 |
| CN | 106308818 | A | 1/2017 |
| CN | 106725524 | A | 5/2017 |
| CN | 109381198 | A | 2/2019 |
| CN | 111419240 | A | 7/2020 |
| CN | 211066647 | U | 7/2020 |
| GB | 2471524 | A | 1/2011 |

* cited by examiner

IMPACT TYPE BLOOD COLLECTION APPARATUS, NEGATIVE PRESSURE BLOOD COLLECTION PEN AND BLOOD COLLECTION METHOD

TECHNICAL FIELD

The present invention relates to the technical field of medical instruments, and in particular to an impact type blood collection apparatus, a negative pressure blood collection pen and a blood collection method.

BACKGROUND ART

A blood collection pen for peripheral blood collection is a common medical instrument used in conjunction with a disposable blood collection needle. In the prior art, a disposable blood collection needle is usually mounted in a needle stand, and the needle stand drives the blood collection needle to achieve puncture under the driving action of an elastic element.

For example, in a negative pressure painless blood collection pen disclosed in the China National Intellectual Property Administration with publication number CN211066647U, a blood collection needle is mounted in a needle stand, and the blood collection needle can be replaced. In a triggered state, the needle stand moves backwards, so that the route of the needle stand is relatively long, and the friction resistance is large during the route. In addition, every time the blood collection needle is replaced, the needle stand is pressed to the position of the triggered state once, and a needle withdrawing spring is compressed once. Over time, the service life of the needle withdrawing spring is shortened, so that the service life of the blood collection pen is shortened.

SUMMARY OF THE INVENTION

The technical problem to be solved by the present invention is to solve the technical defects of a relatively long running route of a needle stand and ineffective compression of a needle withdrawing spring during the process of replacing a blood collection needle in the prior art.

In order to solve the above technical problem, the technical solution provided by the present invention is as follows: an impact type blood collection apparatus at least includes:

- a base;
- a front cover, a rear end of the front cover being detachably connected to the base, and the front cover and the inside of the base forming a first space;
- a needle stand, the needle stand being located in the first space, a front end of the needle stand being provided with a blood collection needle mounting groove, the needle stand having a first position at the end close to the base and a puncture position at the end away from the base in the first space, and the needle stand being capable of moving axially between the first position and the puncture position;
- a first elastic element, the first elastic element enabling the needle stand to be maintained in the first position, the first elastic element being in an energy storage state when the needle stand is in the puncture position, and the first elastic element driving the needle stand to restore from the puncture position to the first position; and

- an impact block, the impact block at least having a first state in which the impact block is attached to a tail end of the needle stand and a second state in which the impact block is separated from the tail end of the needle stand, the impact block storing energy in the second state and being configured to move from the second state to the first state and then drive the needle stand to move from the first position to the puncture position through impact, and a second elastic element being arranged between the impact block and the needle stand, and the second elastic element being configured to be in an energy storage state when the impact block is in the second state.

In a preferred implementation, the second elastic element is an elastic ring, and the elastic ring is configured to drive the impact block to be attached to the tail end of the needle stand in a natural state.

In a preferred implementation, the side of the impact block away from the needle stand is provided with a first accommodating groove for accommodating the elastic ring, and both sides of the impact block are provided with second accommodating grooves in communication with the first accommodating groove.

In a preferred implementation, the needle stand is provided with a third accommodating groove for accommodating the elastic ring and a through groove which is in communication with the third accommodating groove and accommodates the elastic ring to enter the third accommodating groove.

In a preferred implementation, the first elastic element is a spring.

In a preferred implementation, the front cover includes an inner front cover and an outer front cover nested within each other, and an axial displacement adjusting mechanism is arranged between the inner front cover and the outer front cover.

In a preferred implementation, the axial displacement adjusting mechanism includes:

- at least one elastic arm, arranged on a side wall of the inner front cover;
- a guide convex block, arranged on the side of a free end of the elastic arm facing the outer front cover; and
- a guide groove, arranged on an inner wall of the outer front cover and spirally extending, and the guide convex block being adapted to the guide groove.

In a preferred implementation, a front end of the outer front cover is provided with a puncture hole, and further includes a plurality of vent holes arranged around the puncture hole.

In a preferred embodiment, the negative pressure blood collection pen at least includes:

- the impact type blood collection apparatus;
- a rod body, the rod body being connected to the end of the base away from the front cover, and the rod body being provided with at least one vent hole passing through a side wall of the rod body; and
- a driving mechanism, the driving mechanism at least including a piston and a driving component for driving the piston to move in the rod body along an axial direction, an end of the piston being provided with an adsorption block, the impact block being configured to be capable of being magnetically connected to the adsorption block, a radial direction of the piston and the rod body being sealed, the piston having an armed adsorption position and an initial position in the rod body along the axial direction, the vent hole being located between the armed adsorption position and the initial position of the piston, the driving component being configured to drive the piston to move axially between the armed adsorption position and the initial position, and the driving component at least including a driving rod arranged at a tail end of the rod body and capable of moving axially relative to the rod body, and an elastic structure.

In a preferred implementation, a plurality of axially extending convex strips are arranged on an inner wall of the rod body along a circumferential direction, an axially extending slide groove is formed between adjacent convex strips, one end of the slide groove is open, the end close to a tail end is provided with a limiting part, a top end of the convex strip is provided with a clamping groove, one side of the clamping groove is provided with a first slope, and a step surface of the clamping groove is a second slope.

In a preferred implementation, one side of the piston is connected to a piston rod, and the piston rod is provided with a guide rib adapted to a second guide groove.

In a preferred implementation, the driving component further includes an adapter block, the adapter block includes an adapter block body, a plurality of first slide blocks adapted and connected to the slide groove are axially distributed on the periphery of the adapter block body, and a lower end of the first slide block is provided with a third slope.

In a preferred implementation, the driving rod includes a driving rod body, a plurality of second slide blocks adapted to the slide groove are distributed on an outer wall of the driving rod body along a circumferential direction, and a plurality of tooth grooves for interacting with the bottom ends of the first slide blocks are arranged on an upper end surface of the driving rod body along a circumferential direction.

In a preferred implementation, the elastic structure is a third elastic element sleeved over the piston rod, the third elastic element is in an energy storage state when the piston is in an armed adsorption state, and after the piston in an armed adsorption state is triggered, the third elastic element drives the piston to move to the initial position.

In a preferred implementation, the rod body includes a first rod body and a second rod body connected in sequence, an inner side of the first rod body is provided with an inner partition plate at the end close to the second rod body, the center of the inner partition plate is provided with a first via hole for accommodating the piston rod to pass through, the inner partition plate is further provided with a plurality of second guide grooves extending from the first via hole along a radial direction, and the convex strip is arranged on an inner wall of the second rod body.

A blood collection method for using the negative pressure blood collection pen is provided. The space between a front end of the piston and the puncture hole forms a pressure change cavity, and a negative pressure forming process in the pressure change cavity at least includes:

first stage: the volume of the pressure change cavity rapidly increases, and the pressure change cavity is isolated from the outside; before the start of the first stage, the pressure in the pressure change cavity is equal to the external air pressure; with the change of the volume of the pressure change cavity, a first negative pressure is formed in the pressure change cavity, and the first negative pressure continuously increases with the change of the volume of the pressure change cavity;

second stage: in the second stage, the pressure change cavity is in communication with the outside through the vent hole; and third stage: in the third stage, the volume of the pressure change cavity continues to increase, and in the process of increase of the volume of the pressure change cavity, the external air continuously enters the pressure change cavity from the vent hole, and a second negative pressure is formed.

In a preferred implementation, after the volume of the pressure change cavity increases to a limit position, the external air continues to enter the pressure change cavity under the action of the pressure difference until the pressure in the pressure change cavity is equal to the external pressure.

In a preferred implementation, in the second stage, the volume of the pressure change cavity is 0.2-0.8 times the maximum volume of the pressure change cavity.

In a preferred implementation, before the start of the first stage, a blood collection needle in the negative pressure blood collection pen is in a state to be triggered, and a time node of triggering the blood collection needle in a state to be triggered is after the start of the first stage.

In a preferred implementation, the blood collection needle also has a puncture state, and when the blood collection needle is in the puncture state, the negative pressure forming process in the pressure change cavity is performed from the second half of the first stage to the first half of the third stage.

In a preferred embodiment, an impact type blood collection apparatus at least includes:

a base;

a front cover, a rear end of the front cover being detachably connected to the base, and the front cover and the inside of the base forming a first space;

a needle stand, the needle stand being located in the first space, a front end of the needle stand being provided with a blood collection needle mounting groove, the needle stand having a first position at the end close to the base and a puncture position at the end away from the base in the first space, and the needle stand being capable of moving axially between the first position and the puncture position;

a first elastic element, the first elastic element enabling the needle stand to be maintained in the first position, the first elastic element being in an energy storage state when the needle stand is in the puncture position, and the first elastic element driving the needle stand to restore from the puncture position to the first position;

an impact element, an impact cavity for accommodating the impact element being arranged in the needle stand, and the impact element being located in the impact cavity and being capable of moving axially;

a blocking element, the blocking element being located in an open direction of the impact cavity, and the blocking element being provided with a through hole for accommodating a part of the impact element to pass through; and an impact spring, the impact spring being sleeved over the impact element and located between an impact end of the impact element and the blocking element.

In a preferred implementation, the blocking element is fixedly connected to the needle stand.

In a preferred implementation, the needle stand is provided with a second slot passing through a cavity wall of the impact cavity, the blocking element is provided with an elastic connecting arm extending into the impact cavity, and a free end of the elastic connecting arm is provided with a buckle adapted to the second slot.

In a preferred implementation, the impact type blood collection apparatus further includes an adjusting cover, an axial displacement adjusting mechanism is arranged between the adjusting cover and the base, a first limiting adjusting step is arranged in the adjusting cover, and the needle stand is provided with a second limiting adjusting step configured to adapt to the first limiting adjusting step.

In a preferred implementation, the blocking element is fixedly arranged, and an axial guide mechanism is arranged between the needle stand and the blocking element.

In a preferred implementation, the axial guide mechanism includes an axial guide groove arranged on the blocking element and an axial guide rib arranged on the needle stand.

In a preferred implementation, the impact type blood collection apparatus further includes an adjusting cover, an axial displacement adjusting mechanism is arranged between the adjusting cover and the base, a limiting end surface is arranged at an end of the adjusting cover, the limiting end surface is provided with a puncture through hole for accommodating a puncture needle of a disposable blood collection needle to pass through, and the limiting end surface is configured to limit the displacement of a needle body of the disposable blood collection needle.

In a preferred implementation, a front end of the front cover is provided with a puncture hole and further includes a plurality of vent holes arranged around the puncture hole, and a sealing element is arranged between the front cover and the base.

In a preferred embodiment, a negative pressure blood collection pen at least includes the impact type blood collection apparatus, a rod body and a driving mechanism.

Compared with the prior art, the impact type blood collection apparatus and the negative pressure blood collection pen in the embodiments have the following beneficial effects:

(1) During the process of the impact block moving to a state to be triggered, the needle stand is maintained in the first position, which changes the technical concept that the state of the needle stand in the prior art will change with an armed state to be triggered, so that the route of the needle stand is relatively short, and the puncture stability and puncture accuracy are higher.

(2) During the process of replacing a disposable blood collection needle, especially the process of mounting a disposable blood collection needle, based on structure limiting, the needle stand is maintained in the first position, thereby avoiding the ineffective work of an elastic element and being conducive to prolonging the service life of a blood collection pen.

(3) The movement of the piston and the movement of the driving component in the driving mechanism of the negative pressure blood collection pen are both axial. In this way, during the working process, the eccentric force of each component is avoided as much as possible, and the phenomenon of eccentric wear is reduced. During long-term use, the wear of each component of the negative pressure blood collection pen is relatively small, and the accuracy and the sealing performance are more reliable and durable.

DETAILED DESCRIPTION OF THE INVENTION

In order to make the objectives, technical solutions and advantages of the present invention more clear, the present invention is further described in detail below with reference to the drawings and embodiments. It should be understood that the specific embodiments described herein are only intended to explain the present invention, but are not intended to limit the present invention.

In the description of the present invention, it should be understood that the orientation or position relationships indicated by terms "upper", "lower", "front", "rear", "inner", "outer" and the like are based on orientation or position relationships shown in drawings. The terms are only for the convenience of describing the present invention and simplifying the description, and do not indicate or imply that the specified apparatus or component needs to have a specific orientation and needs to be constructed and operated in the specific orientation, so that the terms cannot be understood as a limitation to the present invention.

In the description of the present invention, it should be noted that the terms "mounting", "connected to" and "connection" should be understood in a broad sense, unless otherwise clearly specified and defined. For example, the connection may be fixed connection, integrated connection or detachable connection, may be internal communication between two components, or may be direct connection or indirect connection through an intermediate. For those of ordinary skill in the art, the specific meanings of the above terms in the present invention can be understood according to specific situations.

Embodiment 1

Figure 1:
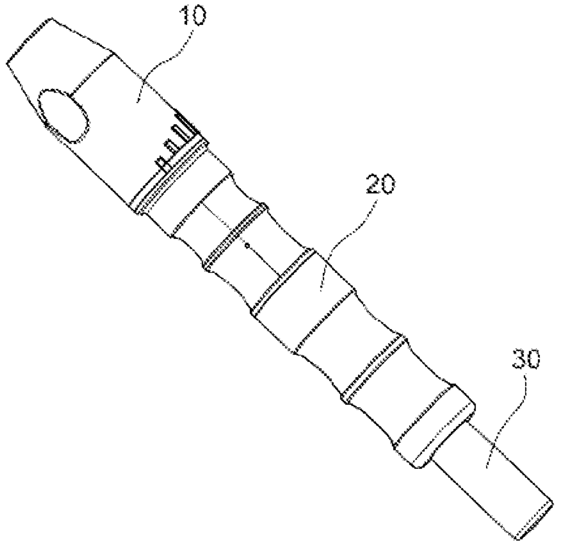
FIG. 1 is a schematic diagram of an external structure of a negative pressure blood collection pen shown in Embodiment 1.

This embodiment provides a negative pressure blood collection pen with a structure as shown in FIG. 1. The negative pressure blood collection pen includes an impact type blood collection apparatus 10, a rod body 20 and a driving mechanism 30.

Figure 2A:
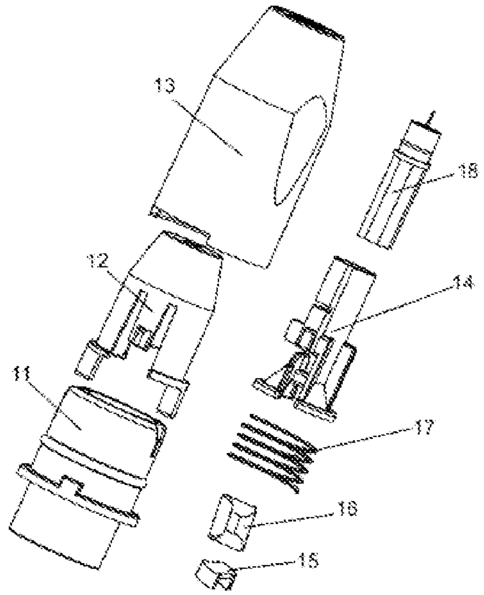
FIG. 2*a* is a schematic structural diagram of an impact type blood collection apparatus in an explosive state in a first implementation in the negative pressure blood collection pen shown in Embodiment 1.
Figure 2B:
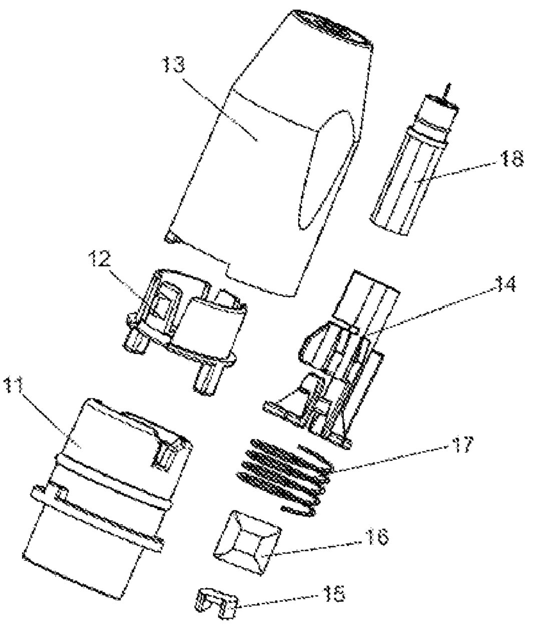
FIG. 2*b* is a schematic structural diagram of an impact type blood collection apparatus in explosive state in a second implementation in the negative pressure blood collection pen shown in Embodiment 1.

As shown in FIG. 2*a* and FIG. 2*b*, the structure of the impact type blood collection apparatus 10 in this embodiment includes a base 11 and a front cover formed by nesting an outer front cover 13 and an inner front cover 12, where the front cover is detachably connected to the base 11.

Figure 7:
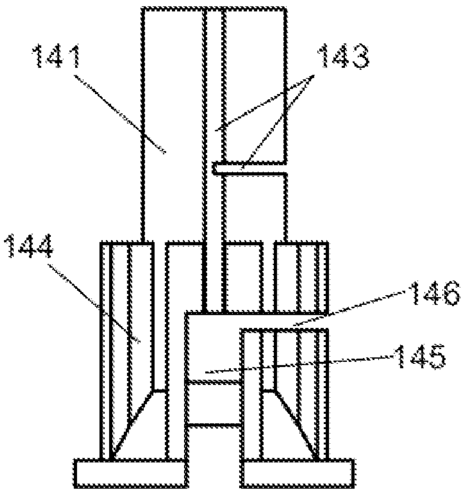
FIG. 7 is a front-view schematic structural diagram of a needle stand in Embodiment 1.
Figure 8:
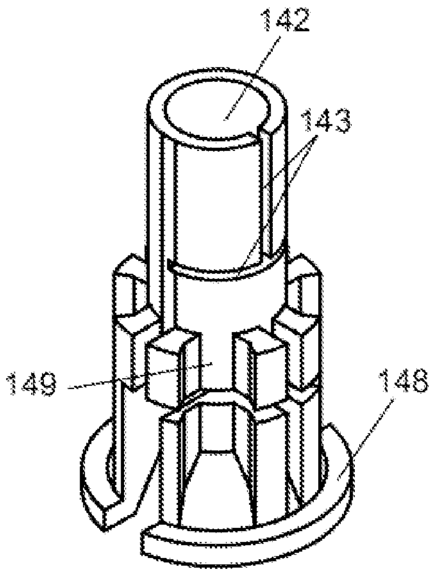
FIG. 8 is a three-dimensional schematic structural diagram of the needle stand in Embodiment 1.
Figure 9:
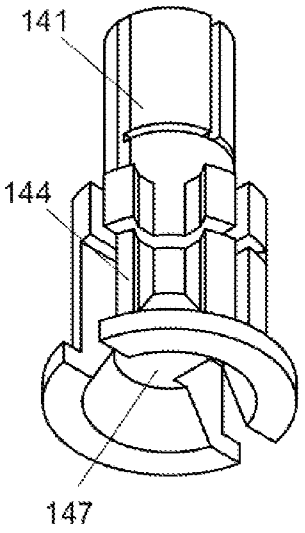
FIG. 9 is a three-dimensional schematic structural diagram of another perspective of the needle stand in Embodiment 1.

In this embodiment, the front cover and the inside of the base 11 form a first space, and a needle stand 14 is mounted in the first space. The needle stand 14 is located in the first space, as shown in FIG. 7 to FIG. 9. The needle stand 14 includes a blood collection needle mounting part 141 and a needle stand body 144, and a front end of the blood collection needle mounting part 141 is provided with a blood collection needle mounting groove 142 for mounting a disposable blood collection needle 18. Preferably, the blood collection needle mounting part 141 is provided with deformation grooves 143 extending along a longitudinal direction and a circumferential direction, and the function of the deformation grooves 143 is to facilitate the disassembly and assembly of the blood collection needle 18.

As shown in FIG. 7 to FIG. 9, an outer wall of the needle stand body 144 in this embodiment is provided with a plurality of first guide grooves 149 distributed along a circumferential direction, a lower end of the needle stand body 144 is provided with a needle stand flange edge 148, and an end surface of the lower end of the needle stand body 144 is further provided with an impact cavity 147 for accommodating an impact block 15.

Figure 10:
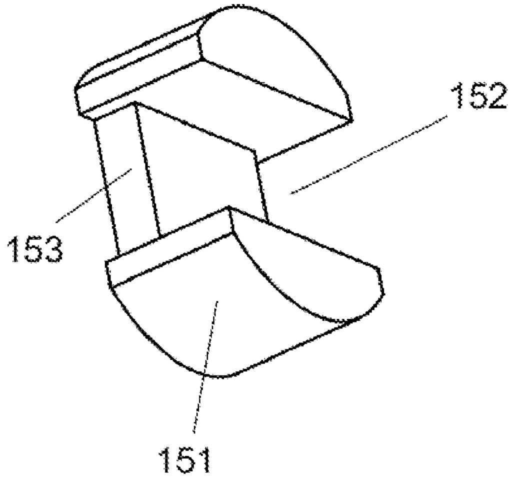
FIG. 10 is a schematic structural diagram of an impact block in Embodiment 1.

As shown in FIG. 10, the impact block 15 in this embodiment includes an impact block body 151, the side of the impact block body 151 away from the needle stand 14 is provided with a first accommodating groove 152 for accommodating an elastic ring 16, and both sides of the impact block are provided with second accommodating grooves 153 in communication with the first accommodating groove 152.

Preferably, in this embodiment, the impact block 15 is connected to the needle stand 14 through the elastic ring 16. The elastic ring 16 is a second elastic element in this embodiment. In a natural state, the elastic ring 16 has the function of driving the impact block 15 to be attached to the tail end of the needle stand, namely the impact cavity. It should be noted that the natural state here does not mean that the elastic ring is not elastically deformed, but means that the elastic ring is not driven by an external force.

Preferably, as shown in FIG. 7 to FIG. 9, the needle stand body 144 is provided with a third accommodating groove 145 for accommodating the elastic ring 16 and a through groove 146 for accommodating the elastic ring 16 to enter the third accommodating groove 145 from a side surface of the needle stand body, and the through groove 146 is in communication with the third accommodating groove 145.

Figure 3:
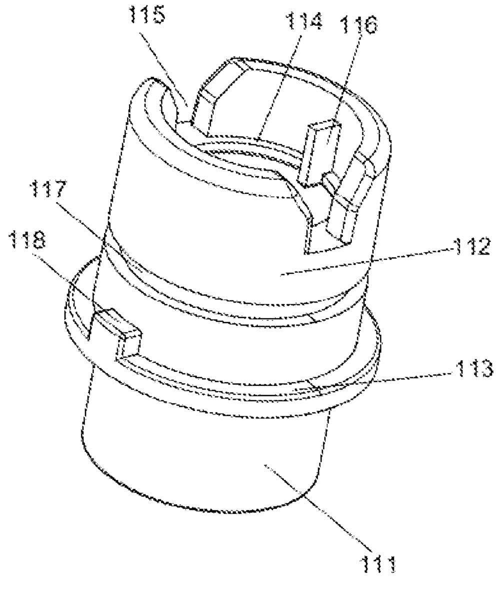
FIG. 3 is a schematic structural diagram of a base in Embodiment 1.

As shown in FIG. 3, the base 11 includes a rod body connecting section 111 configured to connect to the rod body 20, a front cover connecting section 112 configured to connect to the front cover, and a flange lug boss 113 located between the rod body connecting section 111 and the front cover connecting section 112. A front end of the front cover connecting section 112 is provided with two first slots 115 arranged symmetrically, and an inner wall of the front cover connecting section is provided with a limiting ring table 114 and a plurality of axially extending first guide blocks 116. The first guide block 116 is configured to cooperate with the first guide groove 149 to achieve the axial movement guide of the needle stand. An outer wall of the front cover connecting section is provided with a first sealing groove 117.

Figure 19:
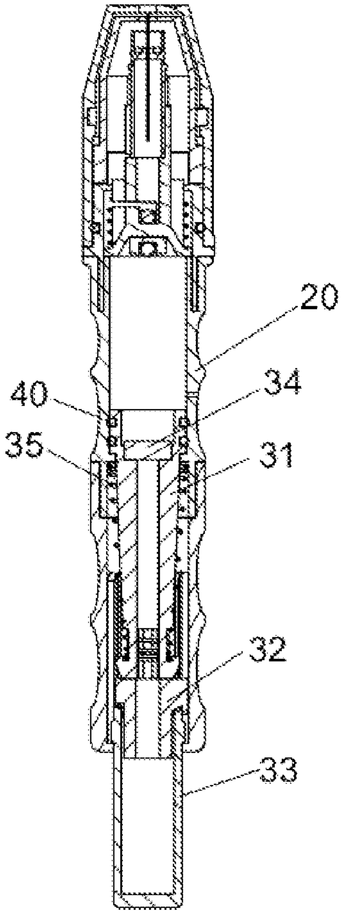
FIG. 19 is a schematic cross-sectional structural diagram of the blood collection pen in an initial state in Embodiment 1.
Figure 20:
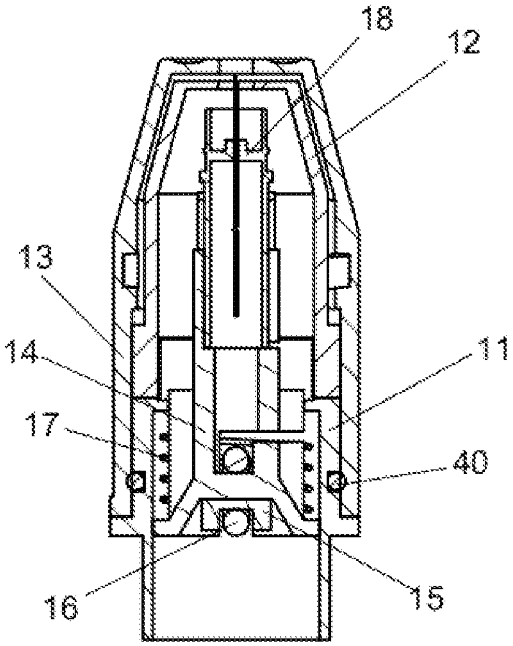
FIG. 20 is a schematic structural diagram of the impact type blood collection apparatus in an initial state in Embodiment 1.
Figure 22:
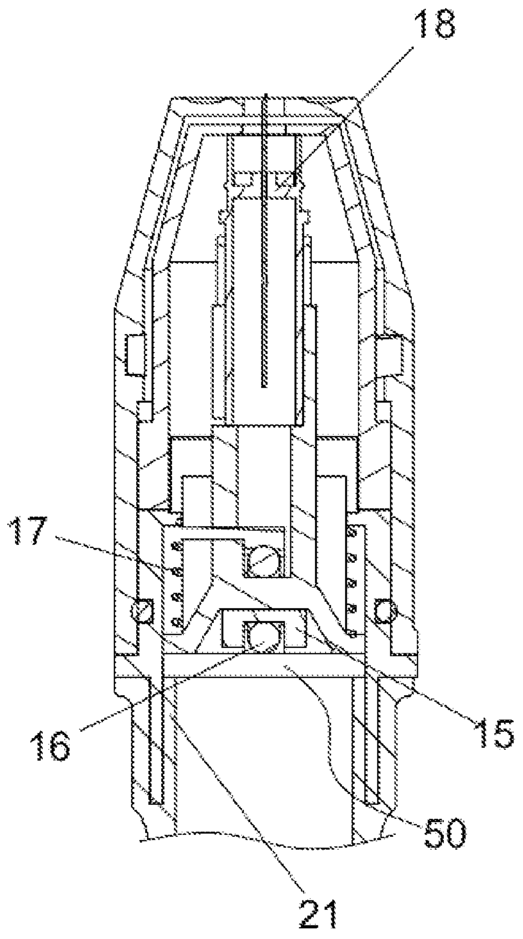
FIG. 22 is a schematic structural diagram of the impact type blood collection apparatus in a puncture state in Embodiment 1.

In this embodiment, the needle stand 14 has a first position at the end close to the base and a puncture position at the end away from the base in the first space, and is configured to be capable of moving axially between the first position and the puncture position. As shown in FIG. 19 and FIG. 20, the needle stand 14 is located in the first position, and based on the function of a first elastic element 17, the needle stand 14 is maintained in the first position. As shown in FIG. 22, the needle stand is located in the puncture position, at this time, the needle stand moves forward by a certain distance from the first position to achieve the puncture of the peripheral skin, and a forward movement space 50 is formed between the tail end of the needle stand and the rod body.

In this embodiment, the first elastic element 17 is preferably a spring, which is sleeved over the needle stand body and is located between the limiting ring table 114 and the needle stand flange edge 148. The first elastic element 17 enables the needle stand to be maintained in the first position. When the needle stand is located in the puncture position, the first elastic element is in a compressed energy storage state. After the puncture is achieved, the compressed potential energy of the first elastic element 17 is released to drive the needle stand to restore from the puncture position to the first position.

In this embodiment, the impact block 15 has a first state in which the impact block is attached to the impact cavity at the tail end of the needle stand and a second state in which the impact block is separated from the tail end of the needle stand. When the impact block is in the second state, the elastic ring is stretched to store energy. After the potential energy generated by stretching the elastic ring is released, the impact block moves from the second state to the first state under the driving action of the elastic ring, and drives the needle stand to move from the first position to the puncture position through impact.

It should be noted that the process of driving the impact block to the driving mechanism separated from the needle stand can be achieved by using different structures. This embodiment will demonstrate a preferred implementation.

In this embodiment, during the process of the impact block moving to a state to be triggered, the needle stand is maintained in the first position, which changes the technical concept that the state of the needle stand in the prior art will change with an armed state to be triggered, so that the route of the needle stand is relatively short, and the puncture stability and puncture accuracy are higher. During the process of replacing a disposable blood collection needle, especially the process of mounting a disposable blood collection needle, based on structure limiting, the needle stand is maintained in the first position, thereby avoiding the ineffective work of an elastic element and being conducive to prolonging the service life of a negative pressure blood collection pen.

In a preferred implementation, the puncture depth of the disposable blood collection needle in this embodiment is controllable. Specifically, an axial displacement adjusting mechanism is arranged between the inner front cover 12 and the outer front cover 13.

In this embodiment, two implementations are provided for the structure of the inner front cover 12, as shown in FIG. 2*a*, FIG. 2*b*, FIG. 4*a* and FIG. 4*b*.

Figure 4A:
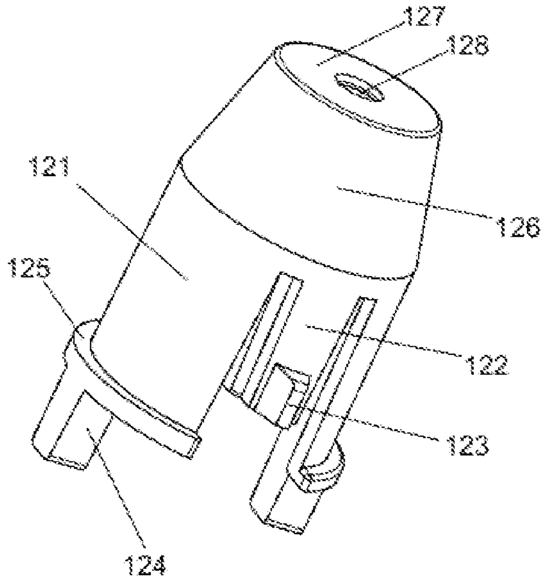
FIG. 4*a* is a schematic structural diagram of an inner front cover in the negative pressure blood collection pen shown in FIG. 2*a*.

In the first implementation, as shown in FIG. 4*a*, the inner front cover includes an inner front cover body 121, a tail end of the inner front cover body 121 is provided with an inner front cover flange edge 125, and the side of the inner front cover flange edge 125 away from the inner front cover body 121 is provided with a first clamping block 124 adapted and connected to the first slot 115. A side wall of the inner front cover body 121 is provided with a pair of elastic arms 122 arranged oppositely, and a free end of the elastic arm 122 is provided with a guide convex block 123 facing one side of the outer front cover.

In this implementation, the end of the inner front cover body 121 away from the inner front cover flange edge 125 is provided with a conical body 126, the conical body 126 is provided with an end surface 127, and the end surface 127 is provided with a needle passing hole 128.

In this implementation, the elastic arm 122 extends from a position close to the conical body 126 to one end of the inner front cover flange edge 125 on the inner front cover body 121.

Figure 4B:
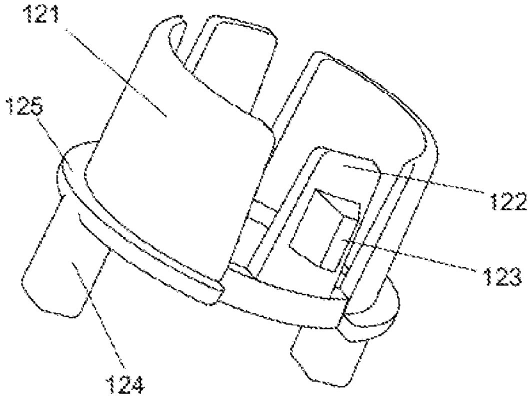
FIG. 4*b* is a schematic structural diagram of an inner front cover in the negative pressure blood collection pen shown in FIG. 2*b*.

In the second implementation of this embodiment, as shown in FIG. 4*b*, the inner front cover includes an inner front cover body 121, a tail end of the inner front cover body 121 is provided with an inner front cover flange edge 125, and the side of the inner front cover flange edge 125 away from the inner front cover body 121 is provided with a first clamping block 124 adapted and connected to the first slot 115. A side wall of the inner front cover body 121 is provided with a pair of elastic arms 122 arranged oppositely, and a free end of the elastic arm 122 is provided with a guide convex block 123 facing one side of the outer front cover.

The difference between this implementation and the first implementation is that the end of the inner front cover body 121 away from the inner front cover flange edge 125 is open, and the conical body 126 in the first implementation is not provided. In this implementation, the elastic arm 122 extends upwards from the position of the inner front cover flange edge 125 on the inner front cover body 121.

Figure 5:
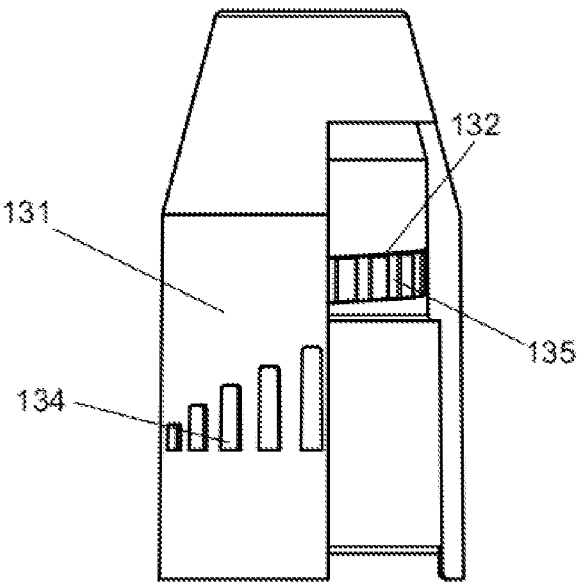
FIG. 5 is a partially sectioned front-view schematic structural diagram of an outer front cover in Embodiment 1.
Figure 6A:
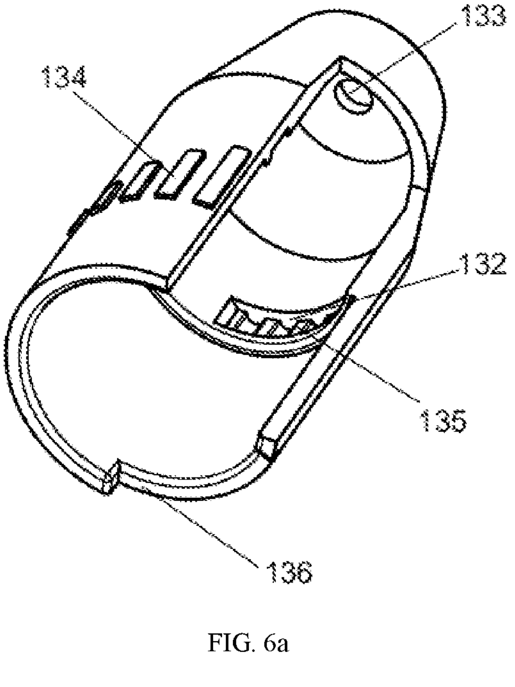
FIG. 6*a* is a partially sectioned three-dimensional schematic structural diagram of the outer front cover in Embodiment 1.

As shown in FIG. 5 and FIG. 6*a*, the outer front cover 13 in this embodiment includes an outer front cover body 131, and a front end of the outer front cover body 131 is provided with a puncture hole 133. It should be noted that a front end of the inner front cover 12 is also provided with a puncture hole corresponding to the position of the puncture hole 133. An inner wall of the outer front cover body 131 is provided with a guide groove 132 extending spirally along an axial direction, and a guide convex block is adapted and connected to the guide groove.

The elastic arm, the guide convex block and the guide groove constitute an axial displacement adjusting mechanism between the inner front cover and the outer front cover in this embodiment. In a case that the relative position of the inner front cover is fixed, the axial displacement of the outer front cover relative to the inner front cover can be adjusted by rotating the outer front cover, so as to achieve the control of the puncture depth.

Preferably, as shown in FIG. 5 and FIG. 6*a*, continuous chock blocks 135 are arranged in the guide groove 132 in this embodiment, and the function of the chock blocks 135 is to provide a clear gear for the puncture depth, so that the control of the puncture depth is more accurate. Especially, during the process of replacing a disposable blood collection needle, the rotation of the outer front cover relative to the inner front cover can be prevented, and even if relative rotation occurs, the corresponding gear can be quickly found and quickly restored.

In addition, in this embodiment, as shown in FIG. 2*a*, FIG. 2*b*, FIG. 3 and FIG. 6*a*, the flange lug boss 113 of the base 11 is provided with a limiting block 118, and the bottom of the outer front cover 13 is provided with a limiting groove 136 corresponding to the limiting block. During the process of controlling and adjusting the puncture depth by rotating the outer front cover, a rotation route is limited. Two limit positions of the limiting block in the limiting groove correspond to a maximum puncture depth and a minimum puncture depth.

Preferably, an outer wall of the outer front cover in this embodiment is further provided with a puncture depth mark 134.

Figure 11:
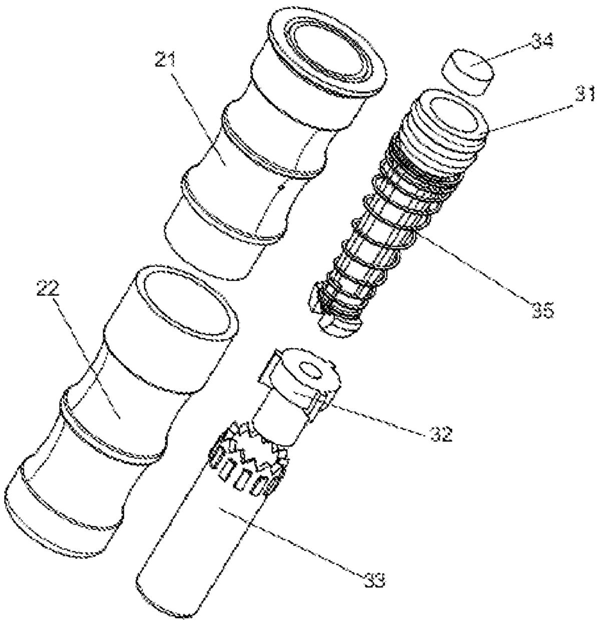
FIG. 11 is a schematic structural diagram of a rod body and a driving mechanism in an explosive state in Embodiment 1.
Figure 12:
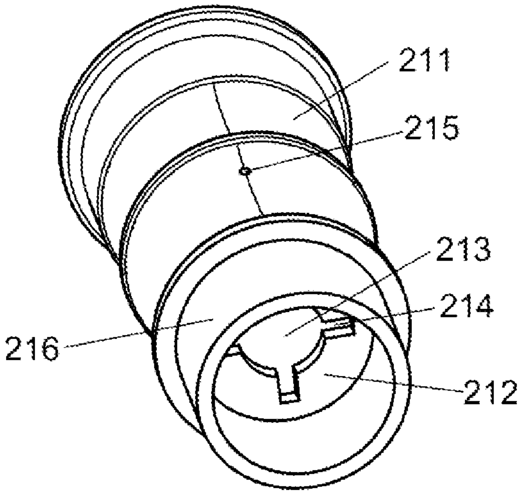
FIG. 12 is a schematic structural diagram of a first rod body in Embodiment 1.
Figure 13:
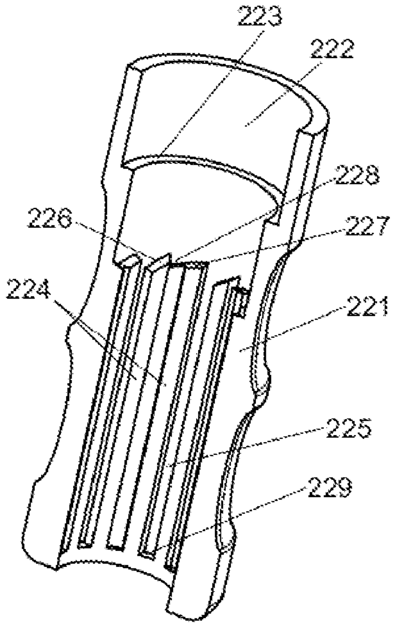
FIG. 13 is a schematic structural diagram of a second rod body in a sectioned state in Embodiment 1.

As shown in FIG. 11, the rod body 20 in this embodiment includes a first rod body 21 and a second rod body 22 connected in sequence. As shown in FIG. 12, the first rod body 21 includes a first rod main body 211, one end of the first rod main body 211 is configured to connect to the base 11, and the other end of the first rod main body is provided with a first rod body connecting part 216 configured to connect to the second rod body 22. The first rod main body 211 is provided with a vent hole 215 passing through a side wall of the first rod main body, an inner side of the first rod main body 211 is provided with an inner partition plate 212 at the end close to the second rod body, the center of the inner partition plate 212 is provided with a first via hole 213, and the inner partition plate is further provided with a plurality of second guide grooves 214 extending from the first via hole along a radial direction.

As shown in FIG. 12, the second rod body 22 in this embodiment includes a second rod main body 221, a front end of the second rod main body 221 is provided with a second rod body connecting hole 222 for accommodating the first rod body connecting part 216, and the hole bottom of the second rod body connecting hole 222 is provided with a limiting step 223.

In this embodiment, a plurality of axially extending convex strips 224 are arranged on an inner wall of the second rod main body 221 along a circumferential direction, an axially extending slide groove 225 is formed between adjacent convex strips 224, the end of the slide groove 225 close to the first rod body is open, and the end of the slide groove close to a tail end of the second rod main body is provided with a limiting part 229. A top end of the convex strip 224 is provided with a clamping groove 228, one side of the clamping groove 228 is provided with a first slope 226, and a step surface of the clamping groove 228 is a second slope 227.

Figure 14:
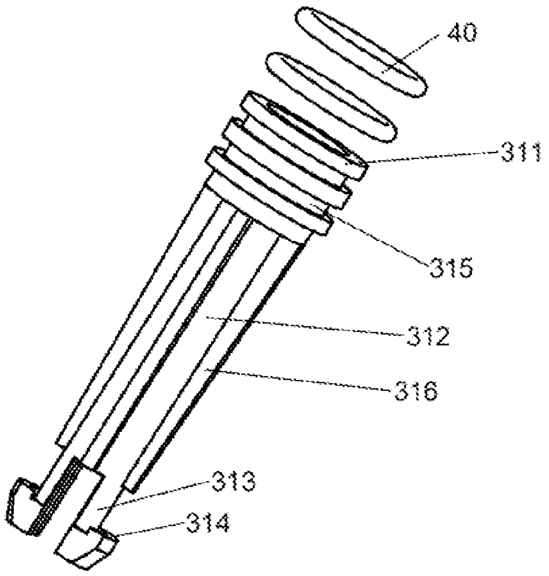
FIG. 14 is a schematic structural diagram of a piston in Embodiment 1.

As shown in FIG. 11, the driving mechanism in this embodiment includes a piston 31, an adapter block 32 and a driving rod 33. As shown in FIG. 14, the piston 31 includes a piston body 311, and the piston body 311 is provided with a second sealing groove 315 for mounting a sealing ring 40. One side of the piston body 31 is connected to a piston rod 312, the piston rod 312 can pass through the first via hole 213, and the piston rod 312 is provided with a guide rib 316 adapted to a second guide groove 214.

In this embodiment, the piston rod is sleeved with a third elastic element 35, and the third elastic element is preferably a spring. In order to facilitate the mounting and limiting of the spring, a free end of the piston rod is provided with a pair of elastic connecting arms 313 arranged oppositely, and free ends of the elastic connecting arms are provided with limiting clamping blocks 314. During disassembly and assembly of the third elastic element, the limiting clamping blocks are gathered to the middle. After mounting, a pair of limiting clamping blocks play a role in limiting the displacement of the third elastic element.

Figure 15:
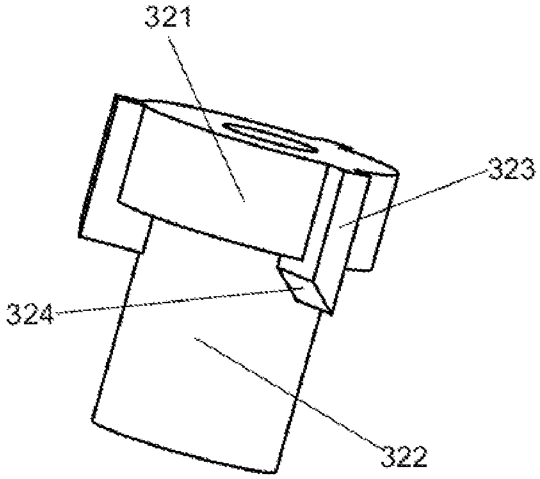
FIG. 15 is a schematic structural diagram of an adapter block in Embodiment 1.

As shown in FIG. 15, the adapter block 32 in this embodiment includes an adapter block body 321, a plurality of first slide blocks 323 adapted and connected to the slide groove 225 are axially distributed on the periphery of the adapter block body 321, and a lower end of the first slide block is provided with a third slope 324. When the third slope 324 interacts with the first slope 226 and the second slope 227, the adapter block is driven to move in both axial and circumferential directions. A lower end of the adapter block body is provided with an adapter connecting rod 322.

Figure 16:
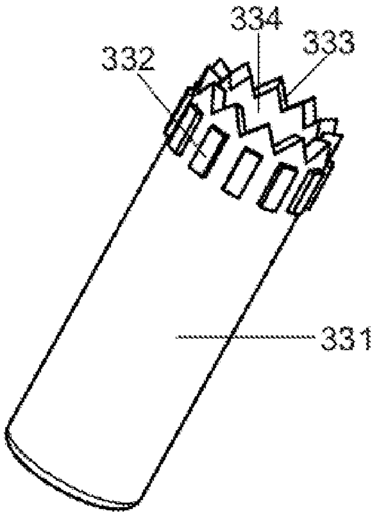
FIG. 16 is a schematic structural diagram of a driving rod in Embodiment 1.

As shown in FIG. 16, the driving rod 33 in this embodiment includes a driving rod body 331, a plurality of second slide blocks 332 adapted to the slide groove 225 are distributed on an outer wall of the driving rod body 331 along a circumferential direction, an upper end of the driving rod body is provided with an adapter connecting cavity 334 in clearance fit with the adapter connecting rod, and a plurality of tooth grooves 333 for interacting with the bottom ends of the first slide blocks 323 are arranged on an upper end surface of the driving rod body along a circumferential direction.

As a special feature of this embodiment, an upper end of the piston body is provided with an adsorption block 34, and the impact block is configured to be capable of being magnetically connected to the adsorption block. In this embodiment, one of the impact block and the adsorption block is made of a magnet material, and the other component is made of a material which can be magnetically adsorbed to the magnet material.

Figure 17:
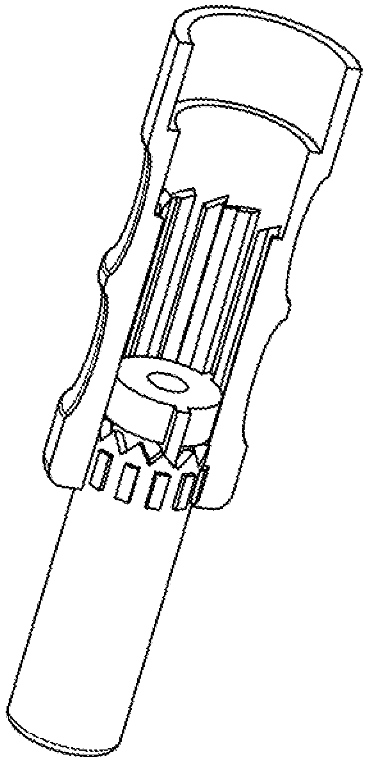
FIG. 17 is a schematic diagram of connection of the second rod body, the adapter block and the driving rod in an initial state in Embodiment 1.

The working process of the negative pressure blood collection pen in this embodiment includes the following steps:

Step 1: The front cover is separated from the base, and the disposable blood collection needle is replaced. After the disposable blood collection needle is replaced, the front cover and the base are mounted together again. The state after mounting is shown in FIG. 17, FIG. 19 and FIG. 20.

Step 2: The driving rod is pushed, the driving rod sequentially transfers an acting force to the adapter block and the piston, and the first slide block pushed onto the adapter block slides out of the slide groove. At this time, one end of the third elastic element is blocked by the inner partition plate, and the other end of the third elastic element is limited by the limiting clamping block to be in a compressed state.

The driving rod is further pushed, and under the double action of the pushing force and the third elastic element, the third slope of the first slide block interacts with the first slope on the convex strip, so that the adapter block performs a resultant movement in axial and circumferential directions until the lower end of the first slide block falls into the clamping groove. In this state, the lower end of the first slide block is limited by the clamping groove, the piston is in a relatively fixed position, and the third elastic element is in a compressed energy storage state. In this state, due to the close distance between the adsorption block and the impact block, under the action of suction, the impact block moves towards the adsorption block until the impact block is connected to the adsorption block by suction. In this state, the elastic ring is stretched to be in a stretched energy storage state.

Figure 18:
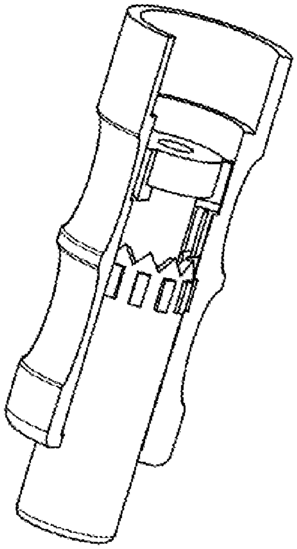
FIG. 18 is a schematic diagram of connection of the second rod body, the adapter block and the driving rod in an armed state to be triggered in Embodiment 1.
Figure 21:
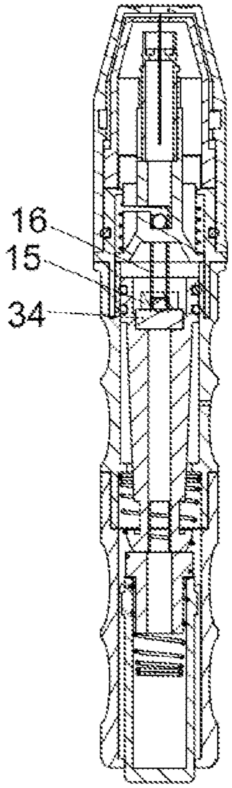
FIG. 21 is a schematic cross-sectional structural diagram of the blood collection pen in an armed state to be triggered in Embodiment 1.

In this way, the negative pressure blood collection pen is in an armed state to be sent, as shown in FIG. 18 and FIG. 21.

Step 3: The position of the puncture hole of the front cover is closely attached to the peripheral skin of a patient to ensure that the puncture hole and the skin are in a basically sealed state. At this time, the puncture action can be completed by pressing the driving rod.

The specific principle is as follows: the driving rod is pressed to drive the third slope of the first slide block to interact with the second slope, the adapter block performs a resultant movement in axial and circumferential directions until the third slope is separated from the second slope, and the first slide block enters the slide groove. In this state, the potential energy of the third elastic element is released to drive the piston, the adapter block and the driving rod to restore to initial states.

During the backward movement of the piston, when the suction force between the impact block and the adsorption block is less than the elastic tension of the elastic ring, the impact block is separated from the piston. Under the action of the restoring force of the elastic ring, the impact block quickly impacts the needle stand, and the impact force drives the needle stand to move forwards to the puncture position shown in FIG. 22.

When the needle stand is located in the puncture position shown in FIG. 22, the first elastic element is compressed to be in an energy storage state. After puncture, the first elastic element drives the needle stand to restore to the first position.

In this embodiment, the space between the front end of the piston and the puncture hole is a pressure change cavity. During the process of triggering the piston in an armed state to be triggered to move backwards, a negative pressure environment is formed in the pressure change cavity, so that the peripheral skin at the puncture hole is sucked out to form a bulge by the negative pressure environment towards the pressure change cavity.

In this embodiment, the negative pressure forming process at least includes:

First stage: During the quick backward movement of the piston under the action of the third elastic element, the volume of the pressure change cavity rapidly increases, and the pressure change cavity is isolated from the outside. Before the start of the first stage, the pressure in the pressure change cavity is equal to the external air pressure. With the change of the volume of the pressure change cavity, a first negative pressure is formed in the pressure change cavity, and the first negative pressure continuously increases with the change of the volume of the pressure change cavity.

Second stage: When the piston moves to the sealing ring and passes through the vent hole, the second stage of this embodiment is formed. In the second stage, the pressure change cavity is in communication with the outside through the vent hole. It should be noted that this stage belongs to a critical state between the first stage and the third stage.

Third stage: after the piston passes through the vent hole, the volume of the pressure change cavity continues to increase, and in the process of increase of the volume of the pressure change cavity, the external air continuously enters the pressure change cavity from the vent hole, and a second negative pressure is formed.

When the piston restores to the initial state, that is, after the volume of the pressure change cavity increases to a limit position, the external air continues to enter the pressure change cavity through the vent hole under the action of the pressure difference until the pressure in the pressure change cavity is equal to the external pressure.

Preferably, in this embodiment, in the second stage, the volume of the pressure change cavity is 0.2-0.8 times the maximum volume of the pressure change cavity.

In this embodiment, before the start of the first stage for forming a negative pressure, a blood collection needle in the negative pressure blood collection pen is in a state to be triggered, and a time node of triggering the blood collection needle in a state to be triggered is after the start of the first stage. When the blood collection needle is in a puncture state, the negative pressure forming process in the pressure change cavity is performed from the second half of the first stage to the first half of the third stage. As a result, the blood inside the skin bulge is collected towards the puncture position so as to facilitate the collection of the required blood at the possible shallowest puncture depth.

Embodiment 2

Figure 6B:
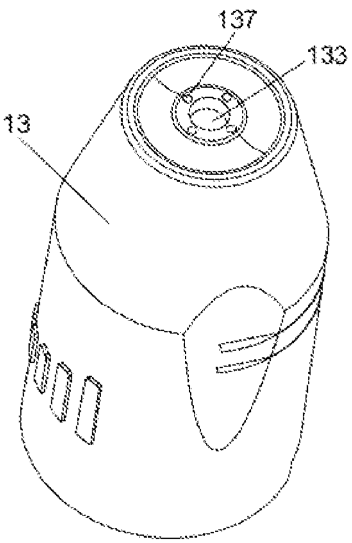
FIG. 6*b* is a three-dimensional schematic structural diagram of an outer front cover in Embodiment 2.

The difference between this embodiment and Embodiment 1 is that the rod body 20 is not provided with a vent hole. As shown in FIG. 6*b*, in this embodiment, four vent holes 137 surrounding the puncture hole 133 are arranged around the puncture hole 133 at the front end of the outer front cover 13. Preferably, the four vent holes 137 are located close to the puncture hole 133 and are uniformly distributed in a circumferential direction.

In this embodiment, the position of the vent hole is changed from the rod body shown in Embodiment 1 to the front end of the outer front cover, which has the following differences:

In Embodiment 1, since the vent hole is located on the rod body and between the armed adsorption position and the initial position of the piston, the negative pressure forming process includes three stages. The disadvantage of this manner is that the rate at which the external air enters the pressure change cavity through the vent hole is constant, that is, the duration of the negative pressure environment in the pressure change cavity is determined. However, for some operators, the negative pressure environment lasts for a long time and is not convenient for self-adjustment, which affects the operation efficiency and the use experience.

In this embodiment, the vent hole is arranged around the puncture hole in the position close to the puncture hole. During the process of blood collection, the front end of the outer front cover is in contact with the skin of a recipient, so that the puncture hole and the vent hole are sealed. After the puncture is achieved, a negative pressure is rapidly formed in the pressure change cavity. However, in this process, no external air automatically enters, the pressure value of the negative pressure is larger, and the stability of the negative pressure environment is better. The skin at the puncture hole has a better blood collection effect due to a larger pressure value and a more stable negative pressure environment.

More importantly, an operator only needs to tilt the negative pressure blood collection pen slightly at an angle to enable some of the vent holes to be in communication with the outside, the external air rapidly enters the pressure change cavity, and the negative pressure environment is relieved. That is, compared with Embodiment 1, the duration of the negative pressure environment can be controlled by the operator, and the direction of tilting the negative pressure blood collection pen may be any direction, so as to adapt to the use habits of different operators.

Embodiment 3

Figure 23:
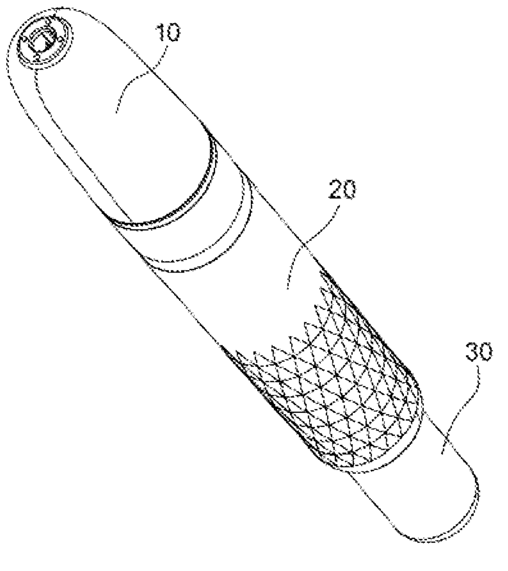
FIG. 23 is a schematic diagram of an external structure of a negative pressure blood collection pen shown in Embodiment 3.

As shown in FIG. 23, a negative pressure blood collection pen in this embodiment at least includes the impact type blood collection apparatus 10, a rod body 20 and a driving mechanism 30. The rod body 20 and the driving mechanism 30 use the corresponding structures or equivalent structures of those in Embodiment 1, which will not be described again in this embodiment.

In the negative pressure blood collection pen in this embodiment, the structure of the impact type blood collection apparatus 10 is different from that in Embodiment 1. The impact type blood collection apparatus 10 is described in detail below.

As shown in FIG. 24 to FIG. 27, the impact type blood collection apparatus 10 in this embodiment includes a base 11, a front cover 13, a needle stand 14, a first elastic element 17 and an adjusting cover 19. A front end of the needle stand 14 is configured to mount a disposable blood collection needle 18, and the disposable blood collection needle 18 includes a needle body 182 and a puncture needle 181.

Figure 31:
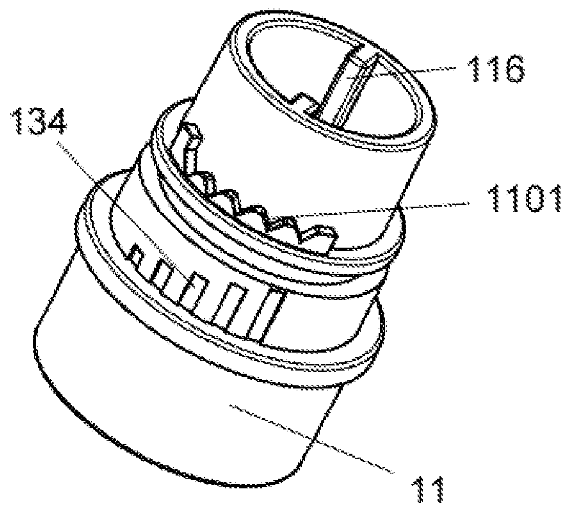
FIG. 31 is a schematic diagram of an external structure of a base in Embodiment 3.
Figure 32:
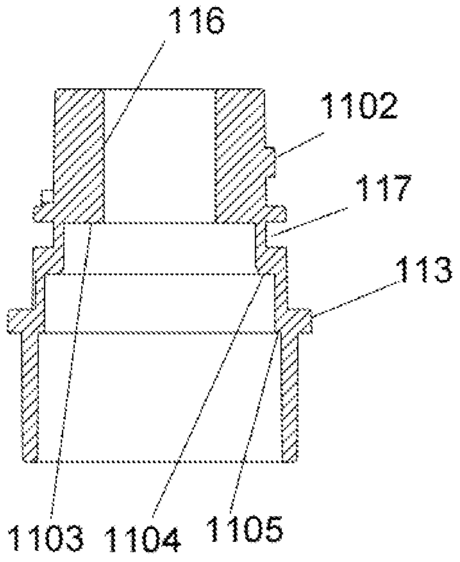
FIG. 32 is a schematic cross-sectional structural diagram of the base shown in FIG. 31.

In this embodiment, the front cover 13 is detachably connected to the base 11. As shown in FIG. 31 and FIG. 32, the base 11 is provided with a first sealing groove 117, and a sealing ring 40 is mounted in the first sealing groove 117 to achieve sealing between the front cover and the base.

As shown in FIG. 32, a first limiting step 1103, a second limiting step 1104 and a third limiting step 1105 are sequentially arranged in the base in this embodiment from top to bottom. The first limiting step 1103 is configured to cooperate with a needle stand flange edge 148 to provide a mounting interval for the first elastic element 17, the second limiting step 1104 is configured to limit the limit displacement of the needle stand flange edge 148, and the third limiting step 1105 is configured to cooperate with the rod body for positioning.

Figure 28:
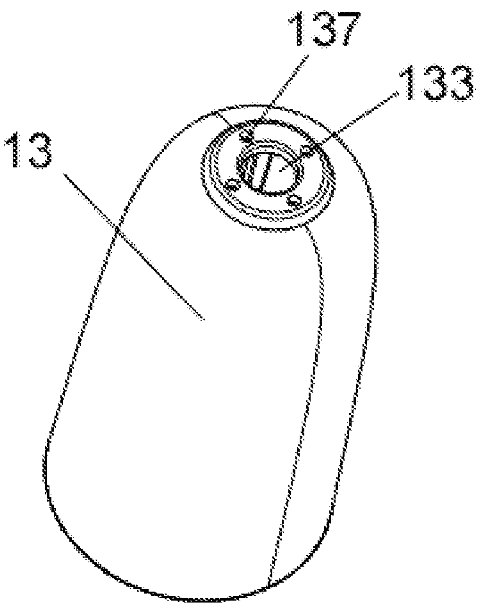
FIG. 28 is a schematic structural diagram of a front cover in Embodiment 3.
Figure 29:
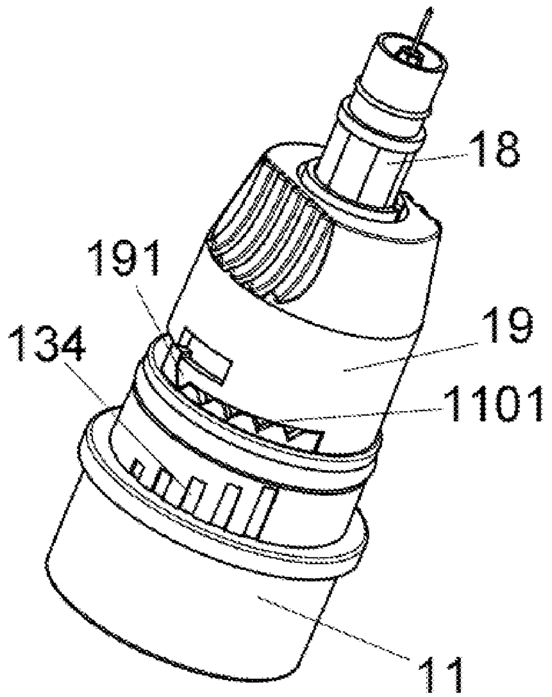
FIG. 29 is a schematic structural diagram of the impact type blood collection apparatus after the front cover is hidden in Embodiment 3.
Figure 30:
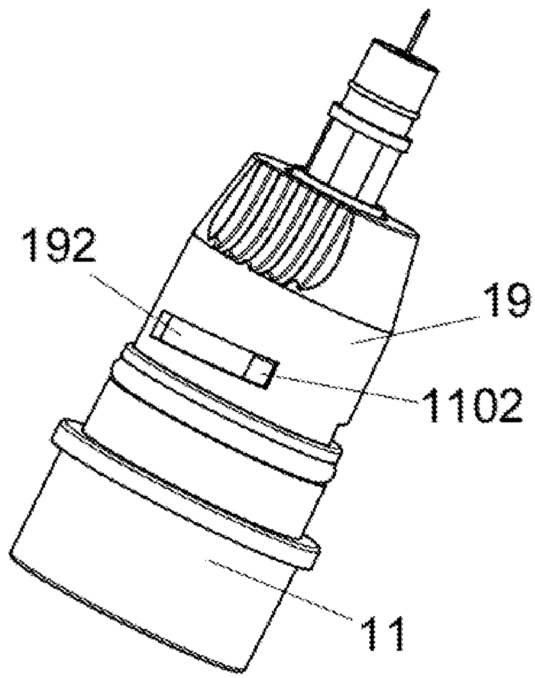
FIG. 30 is a schematic structural diagram of a back of the structure shown in FIG. 29.

As shown in FIG. 28, the structure of the front cover 13 in this embodiment is shown in Embodiment 2, and four vent holes 137 surrounding the puncture hole 133 are arranged around the puncture hole 133 at the front end of the front cover. Correspondingly, in this embodiment, the rod body 20 is not provided with a vent hole.

Figure 26:
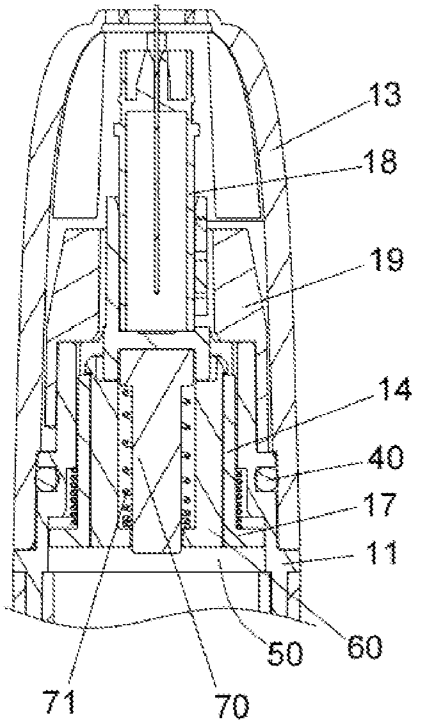
FIG. 26 is a schematic structural diagram of the impact type blood collection apparatus in a puncture state in Embodiment 3.
Figure 27:
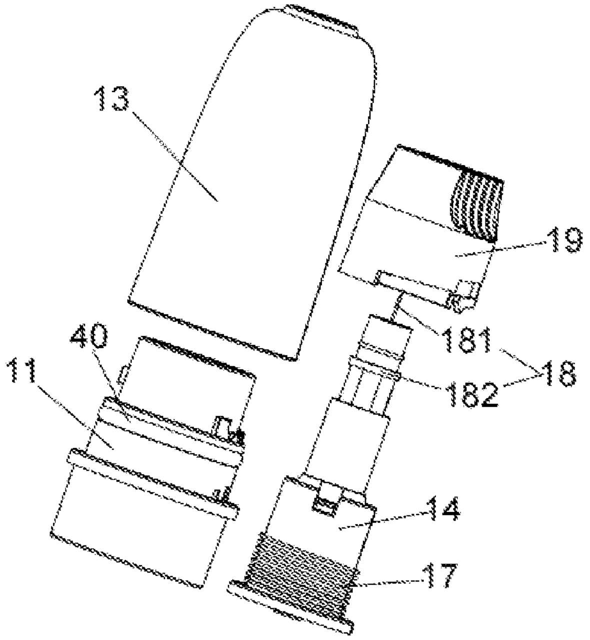
FIG. 27 is a schematic structural diagram of the impact type blood collection apparatus in an explosive state in Embodiment 3.

In this embodiment, the front cover 13 and the inside of the base 11 form a first space, and a needle stand 14 is mounted in the first space. The needle stand 14 is located in the first space, has a first position at the end close to the base as shown in FIG. 24 and a puncture position at the end away from the base as shown in FIG. 26, and can move axially between the first position and the puncture position.

Figure 24:
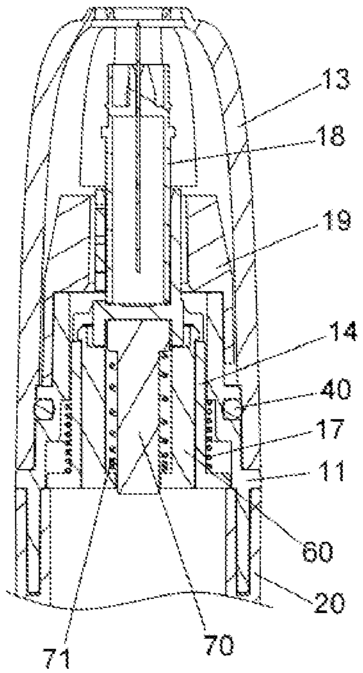
FIG. 24 is a schematic structural diagram of an impact type blood collection apparatus in an initial state in Embodiment 3.

As shown in FIG. 24, the needle stand 14 is located in the first position, and based on the function of the first elastic element 17, the needle stand 14 is maintained in the first position. As shown in FIG. 26, the needle stand is located in the puncture position, at this time, the needle stand moves forwards by a certain distance from the first position to achieve the puncture of the peripheral skin, and a forward movement space 50 is formed between the tail end of the needle stand and the rod body.

In this embodiment, the first elastic element 17 is preferably a spring, which is sleeved over the needle stand body and is located between the first limiting step 1103 of the base and the needle stand flange edge 148. The first elastic element 17 enables the needle stand to be maintained in the first position. When the needle stand is located in the puncture position, the first elastic element is in a compressed energy storage state. After the puncture is achieved, the compressed potential energy of the first elastic element 17 is released to drive the needle stand to restore from the puncture position to the first position.

Figure 34:
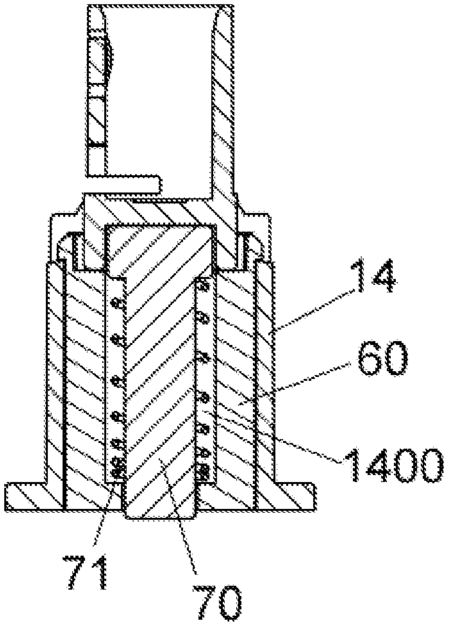
FIG. 34 is a schematic diagram of assembly of a needle stand, a blocking element and an impact element in Embodiment 3.
Figure 35:
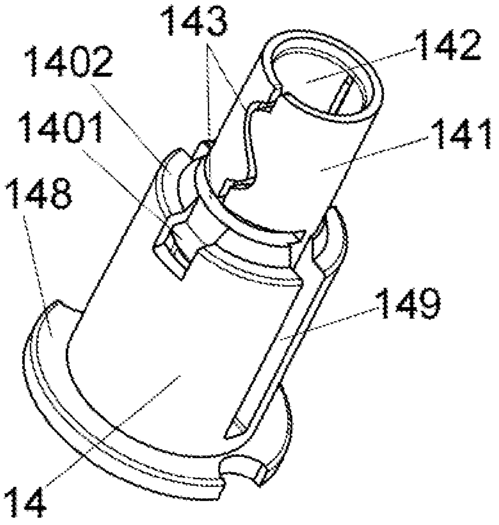
FIG. 35 is a schematic structural diagram of the needle stand in Embodiment 3.

As shown in FIG. 34 and FIG. 35, an impact cavity 1400 is arranged in the needle stand 14 in this embodiment, and a lower end of the impact cavity 1400 is open. An upper end of the needle stand 14 is provided with a blood collection needle mounting part 141, and a front end of the blood collection needle mounting part 141 is provided with a blood collection needle mounting groove 142 for mounting a disposable blood collection needle 18. Preferably, the blood collection needle mounting part 141 is provided with deformation grooves 143 extending along a longitudinal direction and a circumferential direction, and the function of the deformation grooves 143 is to facilitate the disassembly and assembly of the blood collection needle 18.

In this embodiment, as shown in FIG. 35, an outer wall of the needle stand is provided with a plurality of first guide grooves 149 distributed along a circumferential direction. Correspondingly, as shown in FIG. 31 and FIG. 32, first guide blocks 116 adapted to the first guide grooves 149 are arranged inside the base.

Figure 37:
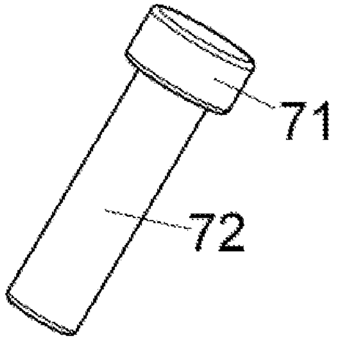
FIG. 37 is a schematic structural diagram of the impact element in Embodiment 3.

In this embodiment, as shown in FIG. 37, the structure of an impact element 70 configured to be mounted in the impact cavity 1400 includes an impact section 71 and a guide section 72. An end surface of a free end of the impact section 71 is configured to cooperate with the cavity bottom of the impact cavity 1400.

In this embodiment, the impact type blood collection apparatus further includes a blocking element 60. The blocking element 60 is fixedly connected to the needle stand, moves synchronously with the needle stand, and is configured to mount the impact element 70 in the impact cavity 1400.

Figure 36:
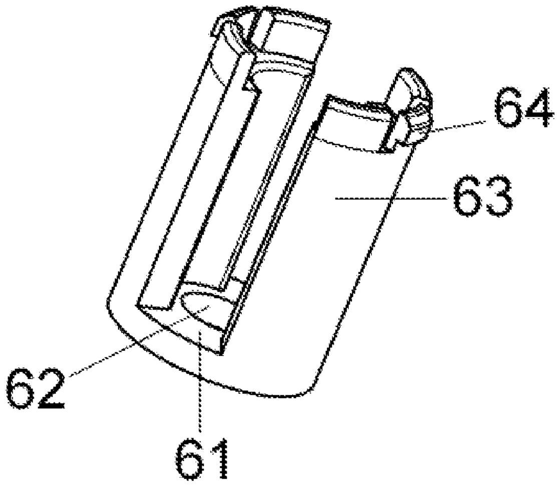
FIG. 36 is a schematic structural diagram of the blocking element in Embodiment 3.

As shown in FIG. 36, in this embodiment, the blocking element 60 includes a blocking partition plate 61 located in an open direction of the impact cavity, a pair of elastic connecting arms 63 extending into the impact cavity, and buckles 64 arranged at free ends of the elastic connecting arms 63. Correspondingly, as shown in FIG. 35, the needle stand is provided with second slots 1401 passing through the cavity wall of the impact cavity, and the buckles 64 are adapted and connected to the second slots 1401 to achieve the fixed connection between the blocking element and the needle stand.

In this embodiment, the blocking partition plate 61 is provided with a through hole 62 for accommodating the guide section 72 to pass through.

In this embodiment, the impact type blood collection apparatus further includes an impact spring 71. As shown in FIG. 34, the impact spring 71 is sleeved over the guide section 72 of the impact element and is located between the impact section 71 and the blocking partition plate 61. At least the material of the guide section 72 can be magnetically absorbed to the adsorption block 34.

Figure 25:
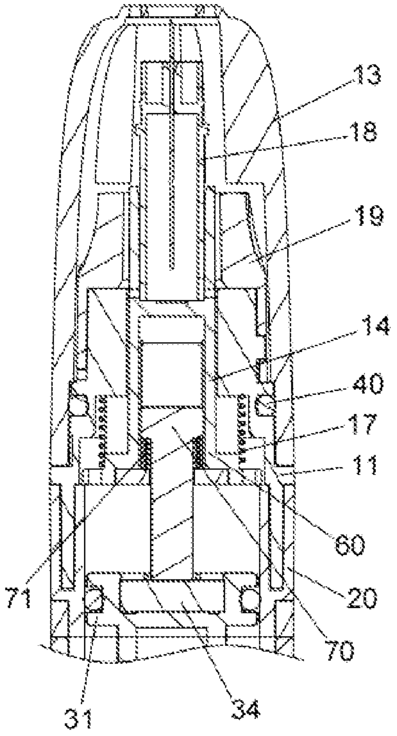
FIG. 25 is a schematic cross-sectional structural diagram of the impact type blood collection apparatus in an armed state to be triggered in Embodiment 3.

As shown in FIG. 25, after the impact element is absorbed by the adsorption block 34, the impact spring 71 is in a compressed energy storage state. After the piston moves backwards to separate the adsorption block 34 from the impact element, the potential energy of the impact spring 71 is released. Based on the release of the potential energy of the impact spring 71, the end surface of the free end of the impact section 71 impacts the cavity bottom of the impact cavity 1400. After impact, the impact element and the needle stand move forwards synchronously to drive the needle stand to move from the first position shown in FIG. 25 to the puncture position shown in FIG. 26.

Compared with the structural form of the impact block and the elastic ring in Embodiment 1, in the impact type blood collection apparatus in this embodiment, since the impact element is always located in the impact cavity of the needle stand, through the guide cooperation between the guide section and the through hole of the blocking element, the axial movement accuracy is higher, and the impact stability is better.

In this embodiment, the impact type blood collection apparatus further includes an adjusting cover 19, and an axial displacement adjusting mechanism is arranged between the adjusting cover 19 and the base to adjust the puncture depth.

Figure 33:
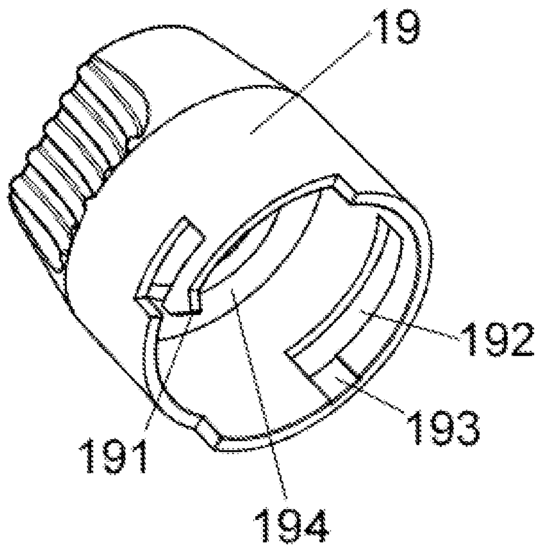
FIG. 33 is a schematic structural diagram of an adjusting cover in Embodiment 3.

As shown in FIG. 29 to FIG. 33, the axial displacement adjusting mechanism in this embodiment includes an adjusting convex part 1102 arranged on an outer wall of the base and a spiral groove 192 which is arranged on the adjusting cover 19 and rises spirally. As shown in FIG. 33, an inner wall of the adjusting cover is provided with an inlet groove 193 for accommodating the adjusting convex part 1102 to enter the spiral groove 192 from a port.

In this embodiment, by rotating the adjusting cover, based on the position changes of the adjusting convex part 1102 and the spiral groove 192, the axial displacement of the adjusting cover is changed.

In this embodiment, in order to set a fixed gear for the puncture depth, the axial displacement adjusting mechanism also includes a plurality of gear teeth 1101 protruding from the side wall of the base, and clamping teeth 191 arranged on the adjusting cover to cooperate with the gear teeth 1101, the clamping teeth 191 are arranged on the elastic arms, and cooperation positions can be switched between the gear teeth 1101 through elastic deformation.

The cooperation between the gear teeth 1101 and the clamping teeth 191 not only sets a fixed gear for the puncture depth, but also provides intuitive hand feeling and sound feedback to an operator during the process of adjusting the gear.

In this embodiment, a first limiting adjusting step 194 is arranged in the adjusting cover 19, and the needle stand is provided with a second limiting adjusting step 1402 configured to adapt to the first limiting adjusting step 194. In a puncture state shown in FIG. 26, the first limiting adjusting step 194 is in contact with the second limiting adjusting step 1402 to control the puncture depth of the disposable blood collection needle.

Preferably, an outer wall of the base in this embodiment is further provided with a puncture depth mark 134.

In Embodiment 1, since during the process of replacing the disposable blood collection needle, the front cover needs to be removed, and the front cover is composed of the inner front cover and the outer front cover. In the process of removing the front cover, due to different operation habits of different operators, there is a risk of causing the outer front cover to rotate relative to the inner front cover. The axial displacement adjusting mechanism in Embodiment 1 is arranged between the outer front cover and the inner front cover, the set puncture depth can be adjusted unconsciously.

In this embodiment, due to the arrangement of the adjusting cover, the axial displacement adjusting mechanism is arranged between the adjusting cover and the base. When the disposable blood collection needle is replaced, in the process of removing or mounting the front cover, the axial displacement adjusting mechanism can not be triggered, so that the operation safety and stability are better.

Embodiment 4

A negative pressure blood collection pen in this embodiment at least includes the impact type blood collection apparatus 10, a rod body 20 and a driving mechanism 30. The rod body 20 and the driving mechanism 30 use the corresponding structures or equivalent structures of those in Embodiment 1, which will not be described again in this embodiment.

The biggest difference between the impact type blood collection apparatus 10 in this embodiment and the impact type blood collection apparatus in Embodiment 3 is that a blocking element 60 and a needle stand 14 are of a separated structure.

Figure 46:
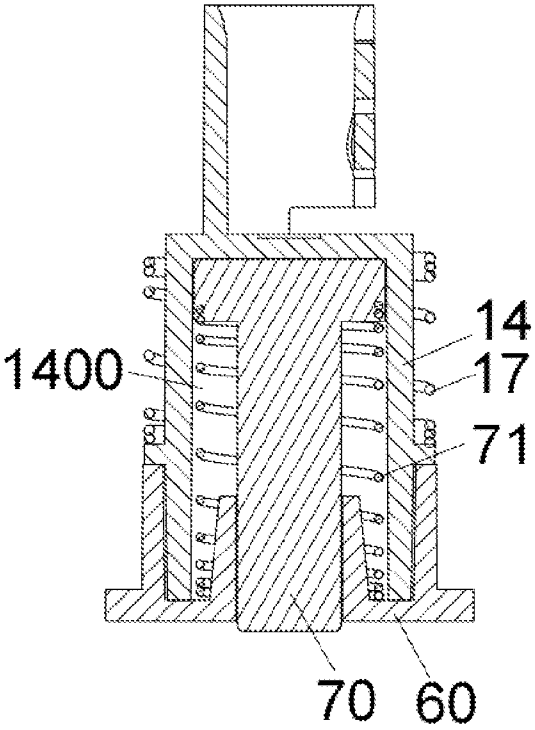
FIG. 46 is a schematic diagram of assembly of a needle stand, a blocking element and an impact element in Embodiment 4.
Figure 47:
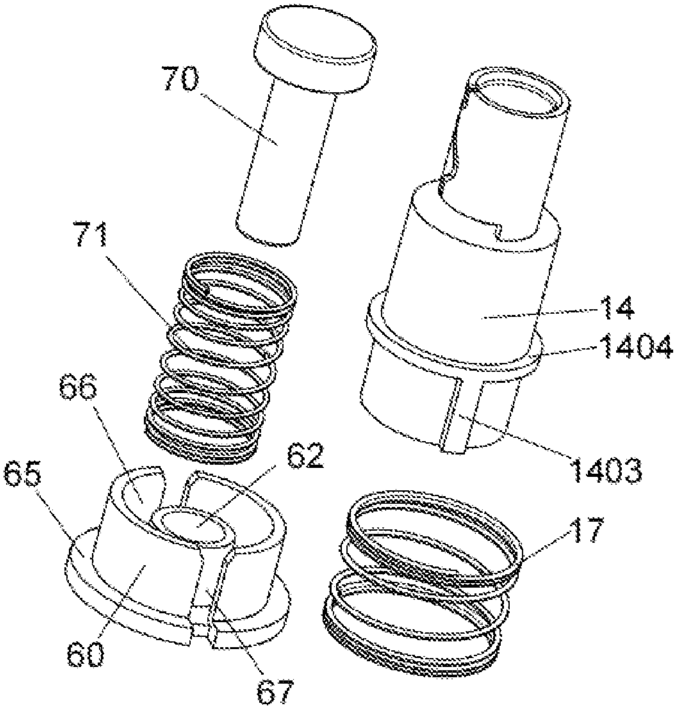
FIG. 47 is a schematic structural diagram of the structure in an explosive state shown in FIG. 46.

As shown in FIG. 46 and FIG. 47, the blocking element 60 is provided with a through hole 62 for accommodating a guide section 72 to pass through, the through hole 62 has a certain axial length, and the periphery is provided with a spring cavity 66 for accommodating an impact spring 71. Further, the blocking element 60 is provided with a blocking flange edge 65.

Figure 38:
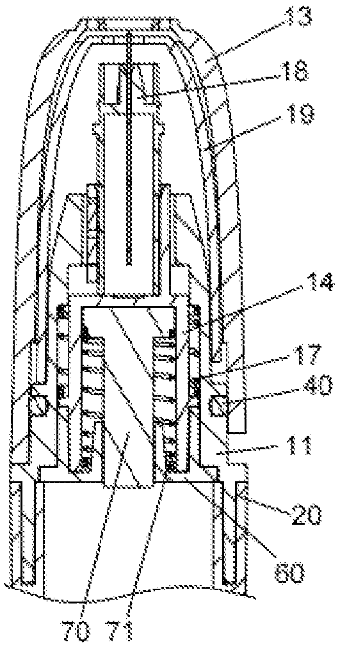
FIG. 38 is a schematic structural diagram of an impact type blood collection apparatus in an initial state in Embodiment 4.
Figure 39:
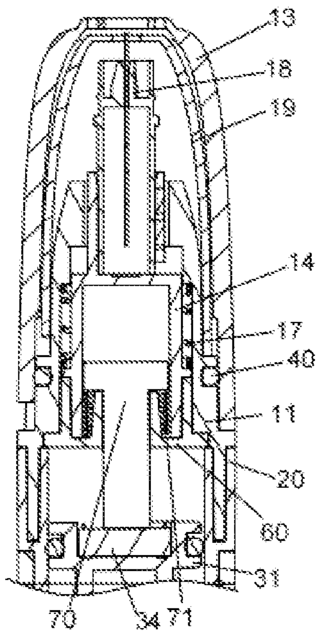
FIG. 39 is a schematic cross-sectional structural diagram of the impact type blood collection apparatus in an armed state to be triggered in Embodiment 4.
Figure 40:
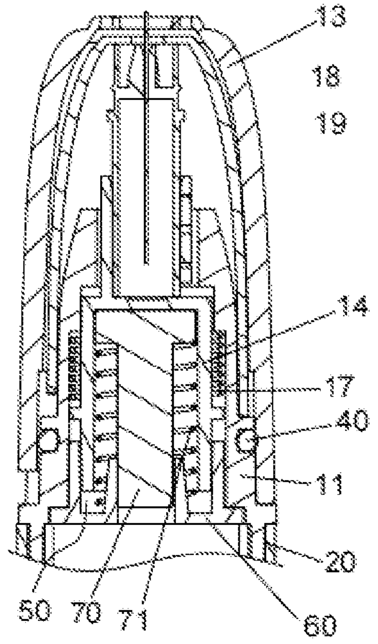
FIG. 40 is a schematic structural diagram of the impact type blood collection apparatus in a puncture state in Embodiment 4.
Figure 41:
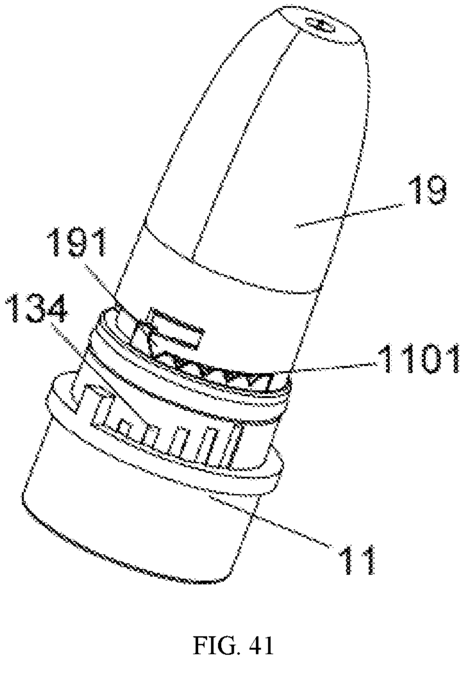
FIG. 41 is a schematic structural diagram of the impact type blood collection apparatus after a front cover is hidden in Embodiment 4.
Figure 42:
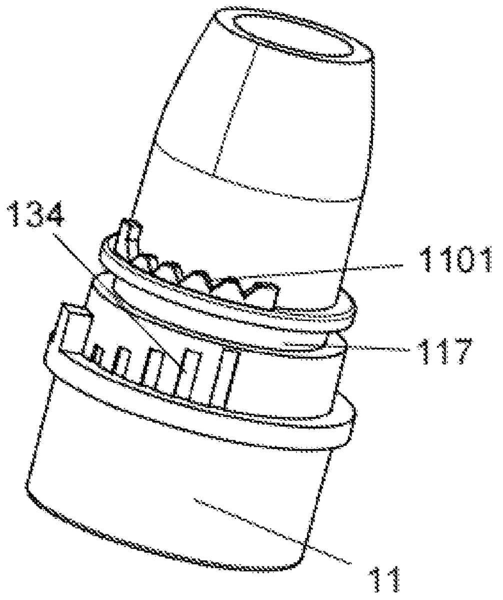
FIG. 42 is a schematic diagram of an external structure of a base in Embodiment 4.
Figure 43:
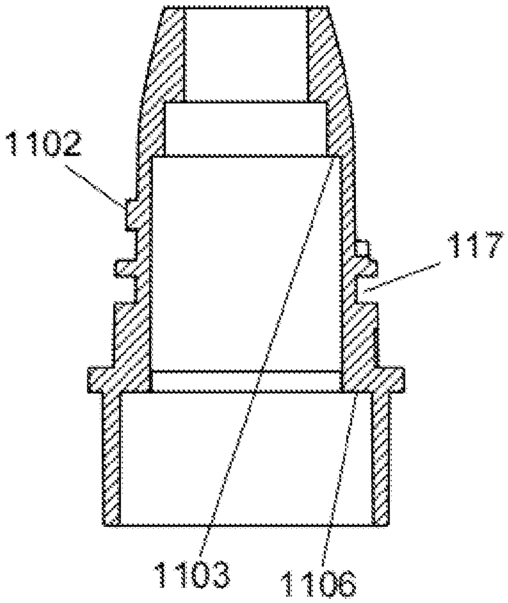
FIG. 43 is a schematic cross-sectional structural diagram of the base shown in FIG. 42.

As shown in FIG. 43, an inner wall of the base is provided with a fourth limiting step 1106 configured to adapt to the blocking flange edge 65. As shown in FIG. 38 to FIG. 40, the blocking flange edge 65 is limited and fixed by the end of the rod body 20 and the fourth limiting step 1106.

Further, in this embodiment, an axial guide mechanism is arranged between the needle stand and the blocking element. Preferably, as shown in FIG. 47, the axial guide mechanism includes a pair of axial guide grooves 67 arranged on the blocking element 60 and a pair of axial guide ribs 1403 arranged on the needle stand, so that the needle stand can only axially move relative to the blocking element to limit the degree of freedom in a circumferential direction.

Further, based on the separated design of the blocking element 60 and the needle stand 14, in this embodiment, the structure of an adjusting cover 19 is different from that in Embodiment 3.

Figure 44:
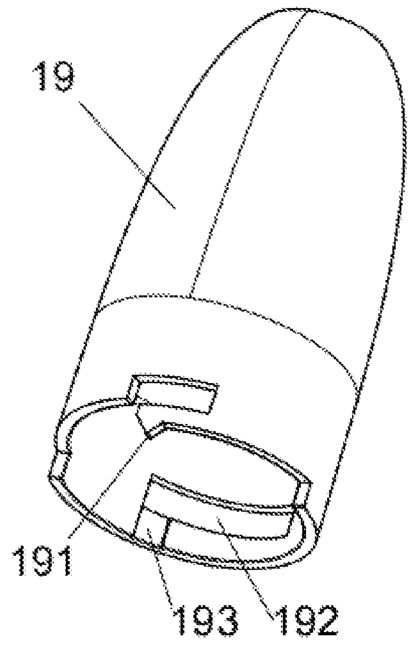
FIG. 44 is a schematic structural diagram of an adjusting cover in Embodiment 4.
Figure 45:
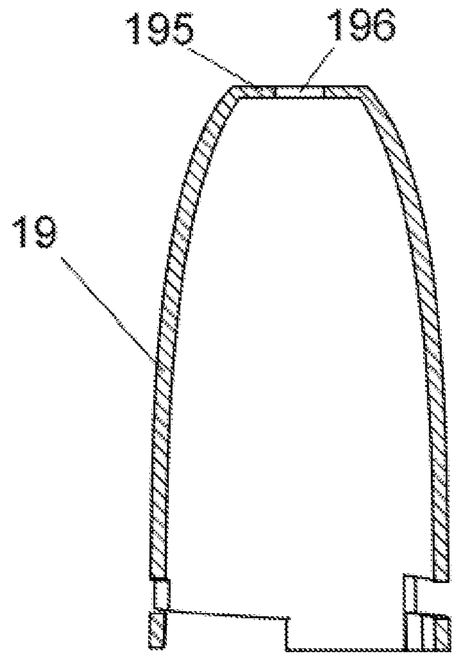
FIG. 45 is a schematic cross-sectional structural diagram of the adjusting cover shown in FIG. 44.

As shown in FIG. 44 and FIG. 45, a limiting end surface 195 is arranged at an end of the adjusting cover 19 in this embodiment, and the limiting end surface 195 is provided with a puncture through hole 196 for accommodating a puncture needle 181 of a disposable blood collection needle 18 to pass through. As shown in FIG. 40, in a puncture state, the limiting end surface 195 is configured to limit the displacement of a needle body 182 of the disposable blood collection needle, thereby achieving the control of the puncture depth.

In this embodiment, an axial displacement adjusting mechanism is also arranged between the adjusting cover and the base. As shown in FIG. 41 to FIG. 44, the axial displacement adjusting mechanism is the same as that in Embodiment 3, which is not described herein again.

In this embodiment, as shown in FIG. 38 to FIG. 40, a first elastic element 17 is located between a first limiting step 1103 of the base and an annular step 1404 of the needle stand. The working process in this embodiment is shown in FIG. 38 to FIG. 40, which is the same as the working process in Embodiment 3. The difference is that in Embodiment 3, the blocking element 60 moves synchronously with the needle stand; but in this embodiment, the blocking element is fixedly arranged, and under the action of the impact element, the impact element moves synchronously with the needle stand.

Compared with Embodiment 3, in this embodiment, the needle stand driven by impact has a lighter weight and requires a smaller impact force.

In a word, the embodiments described above are merely preferred embodiments of the present invention, but are not intended to limit the present invention. Any modification, equivalent replacement and improvement made within the spirit and principle of the present invention shall be included within the scope of the protection of the present invention.

The invention claimed is:

1. An impact type blood collection apparatus, at least comprising:

a base;

a front cover, a rear end of the front cover being detachably connected to the base, and the front cover and the inside of the base forming a first space;

a needle stand, the needle stand being located in the first space, a front end of the needle stand being provided with a blood collection needle mounting groove, the needle stand having a first position at the end close to the base and a puncture position at the end away from the base in the first space, and the needle stand being capable of moving axially between the first position and the puncture position;

a first elastic element, the first elastic element enabling the needle stand to be maintained in the first position, the first elastic element being in an energy storage state when the needle stand is in the puncture position, and the first elastic element driving the needle stand to restore from the puncture position to the first position;

an impact element, an impact cavity for accommodating the impact element being arranged in the needle stand, and the impact element being located in the impact cavity and being capable of moving axially;

a blocking element, the blocking element being located in an open direction of the impact cavity, and the blocking element being provided with a through hole for accommodating a part of the impact element to pass through; and an impact spring, the impact spring being sleeved over the impact element and located between an impact end of the impact element and the blocking element.

2. The impact type blood collection apparatus according to claim 1, wherein the blocking element is fixedly connected to the needle stand.

3. The impact type blood collection apparatus according to claim 2, wherein the needle stand is provided with a second slot passing through a cavity wall of the impact cavity, the blocking element is provided with an elastic connecting arm extending into the impact cavity, and a free end of the elastic connecting arm is provided with a buckle adapted to the second slot.

4. A negative pressure blood collection pen, at least comprising the impact type blood collection apparatus according to claim 3, a rod body and a driving mechanism.

5. The impact type blood collection apparatus according to claim 2, further comprising an adjusting cover, wherein an axial displacement adjusting mechanism is arranged between the adjusting cover and the base, a first limiting adjusting step is arranged in the adjusting cover, and the needle stand is provided with a second limiting adjusting step configured to adapt to the first limiting adjusting step.

6. A negative pressure blood collection pen, at least comprising the impact type blood collection apparatus according to claim 5, a rod body and a driving mechanism.

7. A negative pressure blood collection pen, at least comprising the impact type blood collection apparatus according to claim 2, a rod body and a driving mechanism.

8. The impact type blood collection apparatus according to claim 1, wherein the blocking element is fixedly arranged, and an axial guide mechanism is arranged between the needle stand and the blocking element.

9. The impact type blood collection apparatus according to claim 8, wherein the axial guide mechanism comprises an axial guide groove arranged on the blocking element and an axial guide rib arranged on the needle stand.

10. The impact type blood collection apparatus according to claim 9, further comprising an adjusting cover, wherein an axial displacement adjusting mechanism is arranged between the adjusting cover and the base, a limiting end surface is arranged at an end of the adjusting cover, the limiting end surface is provided with a puncture through hole for accommodating a puncture needle of a disposable blood collection needle to pass through, and the limiting end surface is configured to limit the displacement of a needle body of the disposable blood collection needle.

11. A negative pressure blood collection pen, at least comprising the impact type blood collection apparatus according to claim 10, a rod body and a driving mechanism.

12. A negative pressure blood collection pen, at least comprising the impact type blood collection apparatus according to claim 9, a rod body and a driving mechanism.

13. A negative pressure blood collection pen, at least comprising the impact type blood collection apparatus according to claim 8, a rod body and a driving mechanism.

14. The impact type blood collection apparatus according to claim 1, wherein a front end of the front cover is provided with a puncture hole and further comprises a plurality of vent holes arranged around the puncture hole, and a sealing element is arranged between the front cover and the base.

15. A negative pressure blood collection pen, at least comprising the impact type blood collection apparatus according to claim 14, a rod body and a driving mechanism.

16. A negative pressure blood collection pen, at least comprising the impact type blood collection apparatus according to claim 1, a rod body and a driving mechanism.

* * * * *